(12) United States Patent
Fazleabas

(10) Patent No.: US 7,794,958 B2
(45) Date of Patent: Sep. 14, 2010

(54) METHODS FOR DIAGNOSING ENDOMETRIOSIS

(75) Inventor: Asgerally T. Fazleabas, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 281 days.

(21) Appl. No.: 12/018,010

(22) Filed: Jan. 22, 2008

(65) Prior Publication Data

US 2008/0299676 A1    Dec. 4, 2008

Related U.S. Application Data

(60) Provisional application No. 60/881,300, filed on Jan. 19, 2007.

(51) Int. Cl.
*G01N 33/53* (2006.01)

(52) U.S. Cl. .......................... 435/7.21; 435/2; 435/7.1; 436/501; 436/518; 436/522; 422/50; 422/61; 530/300; 530/350

(58) Field of Classification Search .................. None
See application file for complete search history.

(56) References Cited

U.S. PATENT DOCUMENTS 6,780,594 B2    8/2004    Hess-Stumpp et al.
7,268,117 B2    9/2007    Messer et al.

FOREIGN PATENT DOCUMENTS

WO    WO 2006/116873    11/2006

*Primary Examiner*—Lisa V Cook
(74) *Attorney, Agent, or Firm*—Teddy Scott, Jr.; Todd S. Hofmeister; Polsinelli Shughart PC

(57) ABSTRACT

Provided herein is a method for diagnosing and monitoring endometriosis in a subject by measuring levels of the β-subunit of fibrinogen.

15 Claims, 4 Drawing Sheets

Identification of the β- Subunit of Fibrinogen

Figure 3. The β Subunit of Fibrinogen is Decreased in Uterine Flushings of Baboons with Endometrioses

A.

Controls
1. PA6753
2. PA6677

7022
3. 1 month
4. 3 month
5. 6 month
6. 9 month 6740
7. Self control
8. 7 month
9. 12 month 7162
10. Self control
11. 6 month
12. 12 month 7161
13. Self control
14. 6 month
15. 12 month

B.

1. Control D13PM
2. 8 month. eosis D15PM
3. Spont. eosis D10PO
4. Spont. eosis D8PO

METHODS FOR DIAGNOSING ENDOMETRIOSIS

CROSS-RELATED APPLICATIONS

The present application claims the benefit of the filing date of provisional application 60/881,300, filed on Jan. 19, 2007, which is incorporated by reference in its entirety.

FEDERALLY SPONSORED RESEARCH

This invention was made with government support under National Institute of Child Health and Human Development (NICHD) grant number U54 HD40093. The government has certain rights in the invention.

FIELD OF THE INVENTION

The present invention relates to fibrinogen β-subunit and methods for diagnosing endometriosis.

BACKGROUND

Endometriosis is characterized by the presence of endometrial glands and stroma outside of the uterine cavity and may result from retrograde menstruation. Endometriosis may include a disorder in which abnormal growth of tissue that histologically resembles the endometrium is present in locations other than the uterine lining. Normally, fibrinolysis of the protein fibrinogen may occur during menstruation. Efficient fibrinolysis may result in the production of fragments of β-subunit, which may then be normally passed by the subject. The development of endometriosis may be due to retrograde menstruation where the persistence of fibrin matrices in peritoneal pockets results from hypofibrinolysis, or ineffecient fibrinolysis. Hypofibrinolysis may allow menstrually deposited endometrial fragments to reflux through the fallopian tubes into the peritoneal cavity. Retrograde menstruation occurs in 70-90% of women in the reproductive age group, endometriosis is diagnosed in 10% of this population.

Laparoscopic surgery remains the only accepted means of diagnosis. Thus, there remains a need to develop non-invasive methods of diagnosis. The development of non-invasive methods will eliminate the need of a surgical intervention while shortening the time to diagnosis, which is critical for alleviating pain and improving fertility outcomes.

SUMMARY OF THE INVENTION

Provided herein is a method for diagnosing endometriosis in a subject. The method may comprise providing a sample isolated from a subject and measuring the level of fibrinogen β-subunit in the sample. A level of fibrinogen β-subunit lower than the level of a control may be indicative of endometriosis. The level of fibrinogen β-subunit may be between 0 and 95%, or between 0 and 70% of the level of the control.

The sample may be isolated from a subject. The subject may be a mammal, such as a human. The sample may be blood, lymph fluid, ascetic fluid, gynecological fluid, urine, peritoneal fluid, cerebrospinal fluid, a fluid collected by vaginal rinsing, and/or a fluid collected by vaginal flushing.

The level of fibrinogen β-subunit may be measured by contacting fibrinogen β-subunit with a fibrinogen β-subunit binding partner. The binding partner may be an antibody. The antibody may be polyclonal or monoclonal. The antibody may be a rabbit polyclonal fibrinogen anti-human antibody (Dako Cat. No. A0080), a F4639 monoclonal anti-fibrinogen antibody produced in mouse (Sigma-Aldrich clone FG-21, ascites fluid), a F9902 monoclonal anti-fibrinogen antibody produce in mouse (Sigma-Aldrich clone 85D4, ascites fluid), and/or a anti-fibrinogen antibody produced in goat (Sigma-Aldrich clone F8512, whole antiserum).

The binding partner may comprise a label. The fibrinogen β-subunit may be measured using a detection method such as Western blot, two-dimensional gel electrophoresis, mass spectrometry (MS), tandem mass spectrometry, and/or multiple rounds of mass spectrometry. The mass spectrometric method may use a mass analyzer, such as: an ion trap, a triple quadrupole, time-of-flight, quadrupole-time-of-flight mass spectrometry, and/or Fourier transform ion cyclotron mass spectrometry (FT-ICR-MS). The mass spectrometric method may further use a matrix-assisted laser desorption (MALDI) or electrospray ionization (ESI) ion source.

Also provided herein is a kit for performing a method for diagnosing endometriosis. The kit may comprise an antibody capable of specifically detecting fibrinogen β-subunit and instructions for performing the method of diagnosis.

DETAILED DESCRIPTION

Figure 1:
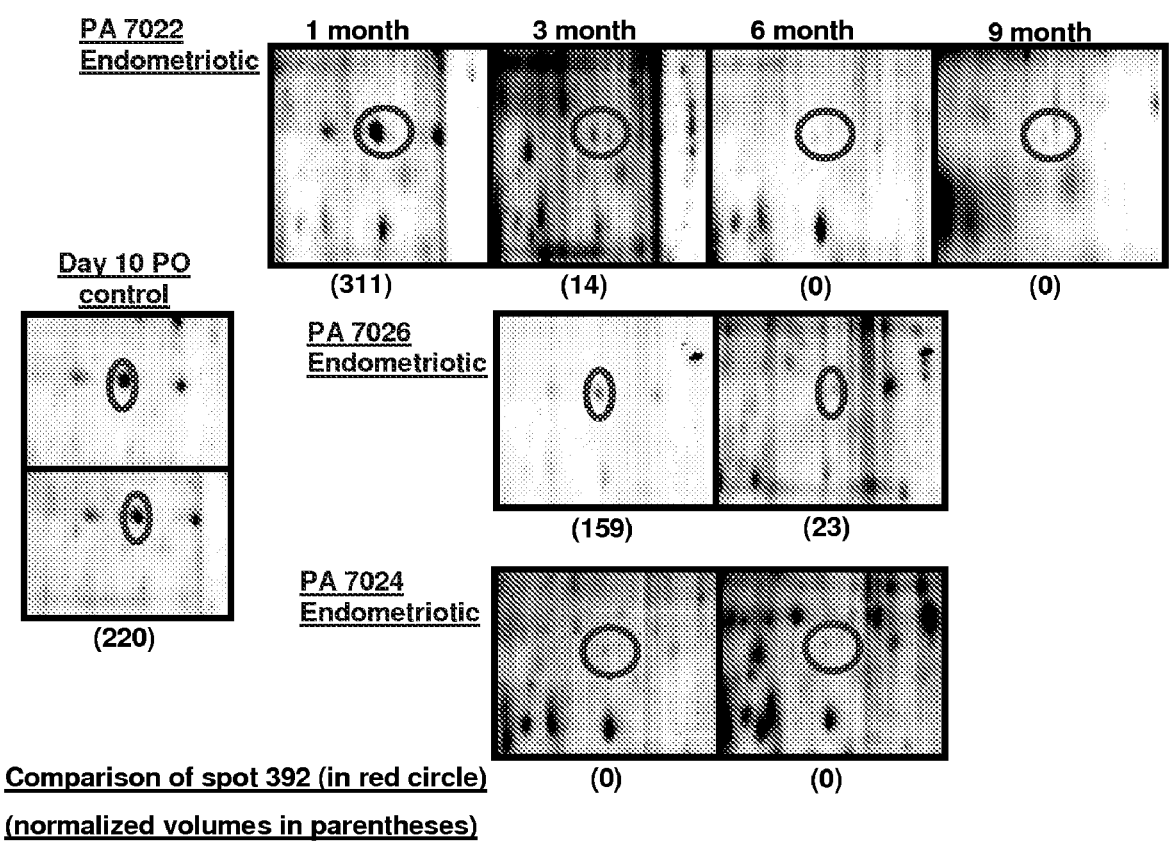
FIG. 1 shows proteonomic analysis of uterine flushings from baboons with endometriosis.

The inventors have made the surprising discovery that the level of fibrinogen's beta subunit ("beta-subunit) decreases, or lowers, or becomes under-abundant in a subject developing or suffering from endometriosis. Previously, diagnostics methods have associated endometriosis with an abundance of fibrinogen β-subunit fragments (see U.S. Pat. No. 7,268,117). Not being bound by theory, endometrial pockets of deposited endometrial β-subunit fragments may lead to the development of a persistent fibrinogen matrix in the endometrium thereby preventing efficient fibrinolysis from occurring and decreasing the level of β-subunit fragments from passing in a subject. The methods described below use non-invasive techniques to measure subunit and identify decrease levels of fibrinogen for purposes of accurately diagnosing endometriosis.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Antibody

"Antibody" as used herein may mean an antibody of classes IgG, IgM, IgA, IgD or IgE, or fragments or derivatives thereof, including Fab, F(ab')2, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The polyclonal antibody may be of mammalian origin, such as human, goat, rabbit, or sheep. The antibody may also be a chimeric antibody. The antibody may be derivatized by the attachment of one or more chemical, peptide, or polypeptide moieties known in the art. The antibody may be conjugated with a chemical moiety. The antibody may be a specific binding member.

b. Attached

"Attached" or "immobilized" as used herein to refer to a polypeptide and a solid support may mean that the binding between the polypeptide and the solid support is sufficient to be stable under conditions of binding, washing, analysis, and removal. The binding may be covalent or non-covalent. Covalent bonds may be formed directly between the polypeptide and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated polypeptide to the streptavidin. Immobilization may also involve a combination of covalent and non-covalent interactions.

c. Fragment "Fragment" as used herein may mean a portion of a reference peptide or polypeptide.

d. Identical

"Identical" or "identity" as used herein in the context of two or more polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

e. Indicator

"Indicator" or "indicator reagent" as used herein may be a composition comprising a label, which is capable of generating a measurable signal that is detectable by external means, and which may be conjugated or attached to a specific binding member for a particular polypeptide. The indicator reagent may be an antibody member of a specific binding pair for a particular polypeptide. The indicator reagent may also be a member of any specific binding pair, including hapten-anti-hapten systems such as biotin or anti-biotin, avidin, or biotin, a carbohydrate or a lectin, a complementary nucleotide sequence, an effector or a receptor molecule, an enzyme cofactor and an enzyme, or an enzyme inhibitor and an enzyme.

f. Label

"Label" or "detectable label" as used herein may mean a moiety capable of generating a signal that allows the direct or indirect quantitative or relative measurement of a molecule to which it is attached. The label may be a solid such as a microtiter plate, particle, microparticle, or microscope slide; an enzyme; an enzyme substrate; an enzyme inhibitor; coenzyme; enzyme precursor; apoenzyme; fluorescent substance; pigment; chemiluminescent compound; luminescent substance; coloring substance; magnetic substance; or a metal particle such as gold colloid; a radioactive substance such as $^{125}I$, $^{131}I$, $^{32}P$, $^{3}H$, $^{35}S$, or $^{14}C$; a phosphorylated phenol derivative such as a nitrophenyl phosphate, luciferin derivative, or dioxetane derivative; or the like. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyases; an isomerase; or a ligase. The enzyme may also be conjugated to another enzyme.

The enzyme may be detected by enzymatic cycling. For example, when the detectable label is an alkaline phosphatase, a measurements may be made by observing the fluorescence or luminescence generated from a suitable substrate, such as an umbelliferone derivative. The umbelliferone derivative may comprise 4-methyl-umbellipheryl phosphate.

The fluorescent or chemiluminescent label may be a fluorescein isothiocyanate; a rhodamine derivative such as rhodamine B isothiocyanate or tetramethyl rhodamine isothiocyanate; a dancyl chloride (5-(dimethylamino)-1-naphtalenesulfonyl chloride); a dancyl fluoride; a fluorescamine (4-phenylspiro[furan-2(3H); lÿ-(3ÿH)-isobenzofuran]-3; 3ÿ-dione); a phycobiliprotein such as a phycocyanine or physoerythrin; an acridinium salt; a luminol compound such as lumiferin, luciferase, or aequorin; imidazoles; an oxalic acid ester; a chelate compound of rare earth elements such as europium (Eu), terbium (Tb) or samarium (Sm); or a coumarin derivative such as 7-amino-4-methylcoumarin.

The label may also be a hapten, such as adamantine, fluoroscein isothiocyanate, or carbazole. The hapten may allow the formation of an aggregate when contacted with a multi-valent antibody or (strep)avidin containing moiety. The hapten may also allow easy attachment of a molecule to which it is attached to a solid substrate.

The label may be detected by quantifying the level of a molecule attached to a detectable label, such as by use of electrodes; spectrophotometric measurement of color, light, or absorbance; or visual inspection.

g. Peptide

A "peptide" or "polypeptide" as used herein may mean a linked sequence of amino acids and may be natural, synthetic, or a modification or combination of natural and synthetic.

h. Sample

"Sample" or "biological sample" as used herein may mean a sample of biological tissue or fluid that comprises a protein. Such samples include, but are not limited to, tissue or fluid isolated from animals. Biological samples may also include sections of tissues such as biopsy and autopsy samples, frozen sections taken for histologic purposes, blood, plasma, serum, sputum, stool, tears, mucus, hair, and skin. Biological samples may also include lymph fluid, ascetic fluid, gynecological fluid, urine, peritoneal fluid, cerebrospinal fluid, a fluid collected by vaginal rinsing, or a fluid collected by vaginal flushing. Biological samples also include explants and primary and/or transformed cell cultures derived from animal or patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

i. Solid Support

"Solid support" or "solid phase" as used herein may be the walls of wells of a reaction tray, test tubes, polystyrene beads, magnetic beads, nitrocellulose strips, membranes, microparticles such as latex particles, and others. The solid support is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid supports include ionic, hydrophobic, covalent interactions and the like. The solid support may also be any material which is insoluble, or may be made insoluble by a subsequent reaction. The solid support may be chosen for its intrinsic ability to attract and immobilize the capture reagent. Alternatively, the solid support may retain an additional receptor which has the ability to attract and immobilize the capture reagent. The additional receptor may include a charged substance that is oppositely charged with respect to the capture reagent itself or to a charged substance conjugated to the capture reagent As yet another alternative, the receptor molecule may be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid support thus may be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid support also may comprise any suitable porous material with sufficient porosity to allow access by detection antibodies and a suitable surface affinity to bind antigens. Microporous structures are generally preferred, but materials with gel structure in the hydrated state may be used as well. Such useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaine earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272, which is incorporated herein by reference.

j. Substantially Identical

"Substantially identical," as used herein may mean that a first and second protein sequence are at least 50%-99% identical over a region of 8-100 or more amino acids.

k. Variant "Variant" as used herein may mean (i) a portion of a referenced protein which may be 8-100 or more amino acids; or (ii) a protein that is substantially identical to a referenced protein. A variant may also be a differentially processed protein, such as by proteolysis, phosphorylation, or other post-translational modification.

2. Diagnosing Endometriosis

Provided herein is a method of diagnosing endometriosis in a subject. The level of β-subunit may be measured from a sample isolated from the subject. The subject sample may have the same level of total protein as the control sample. A level of β-subunit lower than a control may indicate that the subject may have endometriosis. The level of the β-subunit of fibrinogen in a subject may be compared with the level of the β-subunit in a control. The level of the β-subunit may be between 0 and 95%, 0 and 90%, 0 and 80%, 0 and 70%, 0 and 60%, 0 and 50%, 0 and 40%, 0 and 30%, 0 and 20%, or 0 and 10% of the control. There may not be any detectable level of β-subunit in the sample as compared to the control.

a. Sample

The sample may comprise the β-subunit, and may be isolated from endometrial tissue, peritoneal fluid, blood, vaginal secretion or urine of the subject. The sample may be used directly as obtained from the subject or following pretreatment to modify a character of the sample. Pretreatment may include preparing plasma from blood, diluting viscous fluids, and involve filtration, distillation, extraction, concentration, inactivation of interfering components, and/or the addition of reagents.

b. Subject

The subject may be an animal, which may be a warm-blooded animal such as a mammal. The mammal may be afflicted with or suspected of having or being pre-disposed to, or at risk of developing endometriosis. The mammal may be a human or sub-human primate. The human may also be a prepubertal or postpubertal female. The sub-human primate may be a baboon, rhesus monkey, or chimpanzee. The baboon, rhesus monkey, and/or chimpanzee may serve as a useful model system given the high level of conservation of the fibrinogen β-subunit across mammalian species.

c. β-Subunit of Fibrinogen

The β-subunit of fibrinogen may be the 13-chain of fibrinogen, or a variant thereof. The 13-chain may be human, and may have the sequence of GenBank Accession No. P02675 or as set forth in Table 1, or a variant thereof.

TABLE 1

Fibrinogen β-Subunit Sequence

| Sequence | | | | | | SEQ ID NO |
|---|---|---|---|---|---|---|
| 1 mkrmvswsfh | klktmkhlll | lllcvflvks | qgvndneegf | fsarghrpld | kkreeapslr | 1 |
| 61 papppisggg | yrarpakaaa | tqkkverkap | daggclhadp | dlgvlcptgc | qlqeallqqe | |
| 121 rpirnsvdel | nnnveavsqt | ssssfqymyl | lkdlwqkrqk | qvkdnenvvn | eysselekhq | |
| 181 lyidetvnsn | iptnlrvlrs | ilenlrskiq | klesdvsaqm | eycrtpctvs | cnipvvsgke | |
| 241 ceeiirkgge | tsemyliqpd | ssvkpyrvyc | dmntenggwt | viqnrqdgsv | dfgrkwdpyk | |
| 301 qgfgnvatnt | dgknycglpg | eywlgndkis | qltrmgptel | liemedwkgd | kvkahyggft | |
| 361 vqneankyqi | svnkyrgtag | nalmdgasql | mgenrtmtih | ngmffstydr | dndgwltsdp | |
| 421 rkqcskedgg | gwwynrchaa | npngryywgg | qytwdmakhg | tddgvvwmnw | kgswysmrkm | |
| 481 smkirpffpq | q | | | | | | d. Control

The control may be the level of β-subunit in a control sample, which may be a biological sample isolated from a subject who may not have endometriosis. The control sample may have the same level of total protein as a test sample. The total protein may or may not include β-subunit protein. The control subject may not initially have endometriosis. The control subject may develop endometriosis over a period of time. The subject may be female. The female may be fertile. The female may suffer from pelvic pain and not have endometriosis. The control β-subunit may represent a value to which the sample to be tested is compared. The control β-subunit may be at a predetermined amount or level. The control β-subunit may form a binding partner-β-subunit complex that emits a fluorescence level. The binding partner-β-subunit complex may also emit a signal in a calorimetric assay.

The control may also be the amount of fluorescence, calorimetric, or radioactivity emitted by a binding partner-β-subunit complex, given particular amounts of β-subunit and binding partner, and a particular method for detecting the signal emitted by the complex.

The control may be a pre-determined value of the percent decrease of fibrinogen indicative of endometriosis. This pre-determined value is indicative of endometriosis and may be a 10%, 20%, 30%, 40%, 50%, 60%, 70%, 80% or more percent decrease of β-fibrinogen isolated from an individual in comparison to a control. A pre-determined value may be generated by comparing levels of β-fibrinogen isolated from a statistically relevant sample number of individuals who are developing endometriosis and/or suffering from endometriosis and comparing levels of β-fibrinogen to a statistically relevant sample number of β-fibrinogen levels in those that do have endometriosis. Variance in sampling race, age, overall fitness and health, geography, methods of measuring fibrinogen, levels of overall protein measured, types of anti-β-fibrinogen antibodies used, types of dyes or calorimetric markers used, and overall molecular techniques may be used to infuse the overall pre-determined value. The pre-determined value of percent decrease in levels of fibrinogen may then be used against all test samples to diagnosis endometriosis.

3. Measuring β-Subunit

The level of the β-subunit in the sample may be measured by immunohistochemistry, Western blot analysis, solid-phase immunoassay, enzyme-linked immunosorbent assay (ELISA), gel electrophoresis, 2-dimensional (2D) gel electrophoresis, mass spectrometry, or multidimensional protein identification.

a. Immunohistochemistry

The β-subunit may be measured by using immunohistochemical methods, which may be performed on endometrium tissue. The tissue may be fixed.

b. Solid phase immunoassay

The level of the β-subunit may be determined by contacting the sample with a binding partner. The binding partner may be contacted with the sample for time and under conditions sufficient for the formation of a protein/binding partner complex.

The method of determining the level of the β-subunit may comprise contacting the sample with a solid support, binding the β-subunit to the solid support, and contacting the β-subunit with the binding partner bound to a label. This mixture may then be incubated for a time and under conditions sufficient to form a protein/binding partner complex. The level of the β-subunit may be determined by detecting the measurable signal generated by the label. The level of the β-subunit in the sample may be proportional to the signal generated.

The sample may be contacted with the binding partner attached to a solid support. The mixture may be incubated for a time and under conditions sufficient to form a protein/binding partner complex. The mixture may then be transferred to a glass fiber matrix, which may capture the solid support. The mixture may then be contacted with an indicator reagent, which may comprise a second β-subunit binding partner bound to a label. This second binding partner may be an antibody that is monoclonal or polyclonal in nature or a mixture of either. The level of the β-subunit may be determined by detecting the measurable signal generated by the label. The level of the β-subunit in the sample may be proportional to the signal generated.

The sample may also be contacted with the binding partner bound to a label and attached to a solid support. The mixture may be incubated for a time and under conditions sufficient to form a protein/binding partner complex. The mixture may then be contacted with an indicator reagent, which may comprise a second β-subunit binding partner bound to a label. The level of the β-subunit may be determined by detecting the measurable signal generated by the label. The level of the β-subunit may also be determined according to a method as described in U.S. Pat. Nos. 5,795,784 or 5,856,194, the contents of which are incorporated herein by reference. The level of the β-subunit in the sample may be proportional to the signal generated.

The sample may further be contacted with the binding partner attached to a solid support and with an indicator reagent, which may comprise (i) a second β-subunit binding partner and (ii) biotin. The mixture may be incubated for a time and under conditions sufficient to form a protein/antibody complex. The mixture may then be transferred to a glass fiber matrix, which may capture the solid support. The mixture may then be contacted with an indicator reagent bound to a label and comprising an anti-biotin antibody or avidin. The level of the β-subunit may be determined by detecting the measurable signal generated by the label. The level of the β-subunit in the sample may be proportional to the signal generated.

The sample may also be contacted with the binding partner attached to a solid support and with an indicator reagent, which may comprise a second β-subunit binding partner bound to a label. The mixture may be incubated for a time and under conditions sufficient to form a protein/antibody complex. The level of the β-subunit may be determined by detecting the measurable signal generated by the label. The level of the β-subunit in the sample may be proportional to the signal generated.

The sample may further be contacted with the binding partner attached to a solid support. The mixture may be incubated for a time and under conditions sufficient to form a protein/binding partner complex. The mixture may then be contacted with an indicator reagent, which may comprise a second β-subunit binding partner bound to a label. The mixture may be incubated for a second time and under conditions sufficient to form a protein/binding partner complex. The level of the β-subunit may be determined by detecting the measurable signal generated by the label. The level of the β-subunit in the sample may be proportional to the signal generated.

A non-solid phase diagnostic assay may be used in the method. These assays are well-known to those of ordinary skill in the art and are considered to be within the scope of the present invention. Examples of such assays include those described in U.S. Pat. Nos. 5,925,512 or 7,141,242, the contents of which are incorporated herein by reference.

The label may be detected using a detection system, which may comprise a solid support. The solid support may be adapted to be used by a semi-automated or fully automated immunoanalyzer. The detection system may deliver the sample and reagents (which may comprise an antibody, a label, a buffer, or the like) to a reaction vessel, perform incubations, and optionally wash an unbound labeled polypeptide from a bound labeled polypeptide. The detection system may be automated without user intervention once the sample and reagents are inserted into the system. The automated detection system may be distinguished from a manual or less-automated system by the ability of the system to perform at least 8, 16, 64 or 128 assays in a 48-hour period without user intervention. The system may also be able to calculate the concentration or quantity of a polypeptide in the sample automatically, without the need for human calculation or input.

The detection system may also comprise a cartridge format or test strip assay. The detection system may provide unit-dose loadable assay reagents into a disposable instrument, and the unit-dose may contain all the reagents necessary to assay to detect the polypeptide. The disposable instrument may comprise a plastic housing, which may comprise a disposable membrane-like structure of nylon, nitrocellulose, or other suitable material. The sample may be preprocessed or loaded directly onto a loading zone of the disposable instrument. The sample may then optionally flow across the membrane-like structure through a plurality of zones contained on the membrane. The membrane-like structure may further comprise a detergent or lateral flow-aid. The membrane-like structure may also contain an absorbant to collect excess fluid and/or encourage lateral flow across the membrane. The detection system may comprise a multi-pack system in which each pack may comprise sufficient reagents to perform 1, 2, 4, 8, 10, or 12 assays.

The detection system may also comprise a microfluidic device designed to analyze the sample in the microliter range (e.g., less than 4 μL, 12 μL, or 50 μL). The microfluidic device may comprise a flow aids, propulsion device (which may comprise an expansion gel, wax, or gas), nanovalving, or the like to assist the transportation of the sample or assay reagents or both through the microfluidic device.

Of course, it goes without saying that any of the exemplary formats herein, and any assay or kit according to the invention can be adapted or optimized for use in automated and semi-automated systems.

c. Mass Spectrometry, 2D Gel Electrophoresis, and Multi-dimensional Protein Identification The β-subunit may also be detected by one of numerous methods that have been described for analyzing protein compositions. The method may be as described as in WO 00/11208, which discusses mass spectrometric methods for analysis of proteins; Cravatt and Sorenson, *Current Opinion in Chemical Biology* 2000; 4(6):663-8, which discusses chemical strategies for analyzing protein function; U.S. Pat. No. 4,433,051, which discusses the use of α-difluoromethylomithine for use in protein analysis; U.S. Pat. No. 6,127,134, which discusses difference gel electrophoresis using matched multiple dyes; Gygi et al., *Proc. Natl. Acad. Sci. USA* 2000; 97:9390-5, which discusses the use of 2D gel electrophoresis in conjunction with mass spectrometry to analyze proteins; and Aebersold et al., PCT/US99/19415, which discusses digestion of labeled protein samples; the contents of all of which are incorporated herein by reference.

The β-subunit may also be detected by 2D gel electrophoresis (2DE) and the subsequent sequential identification of the separated protein species, by mass spectrometry. The detection method may permit the identification of essentially any protein that may be detectable by conventional protein staining methods including silver staining. For example, the β-subunit may be detected by the 2 DE/MS$^n$ method, which may comprise quantifying proteins by densitometry of stained spots in 2DE gels, followed by mass spectrometry (MS), tandem mass spectrometry (MSMS or MS$^2$), or multiple rounds of mass spectrometry (MS)$^n$. Alternatively, the staining step can be omitted, and the proteins can be detected by mass spectrometry, for example, by analyzing extracts of every slice from a 1D gel, or from every piece of a 2D gel, or by scanning membranes onto which digests from such gels have been deposited by transblotting (Bienvenut et al., *Anal. Chem.* 1999; 71:4800-7).

The β-subunit may be detected by a method as described in U.S. Pat. Nos. 7,183,118 or 7,045,296, which are related to method of protein detection, the contents of which are incorporated herein by reference.

The β-subunit may also be detected by a variety of mass spectrometry system that comprises a mass analyzer with high mass accuracy, high sensitivity and high resolution, such as an ion trap, triple quadrupole, and time-of-flight, quadrupole time-of-flight mass spectrometeres and Fourier transform ion cyclotron mass analyzers (FT-ICR-MS). The mass spectrometers may be equipped with matrix-assisted laser desorption (MALDI) and electrospray ionization (ESI) ion sources, although other methods of peptide ionization may also be used. In ion trap MS, an analyte may be ionized by ESI or MALDI and then put into an ion trap. Trapped ions may then be separately analyzed by MS upon selective release from the ion trap. Fragments may also be generated in the ion trap and analyzed. Sample molecules such as released β-subunit fragments may be analyzed, for example, by single stage mass spectrometry with a MALDI-TOF or ESI-TOF system. The methods of mass spectrometry analysis may be as described in Yates, *Mass Spect.* 1998; 33:1-19; Kinter and Sherman, Protein Sequencing and Identification Using Tandem Mass Spectrometry, John Wiley & Sons, New York, 2000; or Aebersold and Goodlett, *Chem. Rev.* 2001; 101:269-95; the contents of all of which are incorporated herein by reference.

The β-subunit may also be detected using multidimensional protein identification technology (MudPIT). For example, a sample comprising the β-subunit may be prepared, removing any components which may interfere with chromatography. The sample may then applied to an affinity column. Alternatively, the sample may treated with a protease and then applied to the affinity column. Additionally, the sample may be processed prior to application to the affinity column. The sample may also be processed using a method such as chromatography, protein precipitation, and centrifugation.

After the binding of the β-subunit to a functional affinity column, the column may be washed to remove all non-binding proteins. The bound proteins may then be eluted from the affinity column and further processed for mass spectrometry. The preparative treatment of eluted proteins prior to mass spectrometry analysis may rely on further chromatographic separation of peptide fragments generated by proteolysis of the eluted proteins. The resultant peptide mixture can be subjected to one- or multi-dimensional chromatography column prior to mass spectrometry analysis. A high throughput adaptation of such treatment may be MudPIT.

The β-subunit may be treated with a protease prior to MudPIT. The mixture may then be run over a mixed matrix comprising a strong cation exchange matrix stacked with a reverse-phase matrix. The matrices may be stacked such that as proteins are eluted from one matrix they bind to the second. Finally, as the proteins are eluted from the MudPIT column they may immediately be subject to tandem MS and identified by comparing the resultant mass spectra to theoretical mass spectra generated from protein or DNA databases by the SEQUEST algorithm, such as described in U.S. Pat. No. 5,538,897, the contents of which are incorporated herein by reference.

MudPIT may be performed as described in Florens et al., Proteomic Analysis by Multidimensional Protein Identification Technology. Methods in Molecular Biology: New and Emerging Proteomics Techniques. Totowa, N. J.: Humana Press Inc.; 2006; 328:159-175; Swanson et al., The continuing evolution of shotgun proteomics, *Drug Discov Today* 2005; 10:719-725; MacCoss et al., Shotgun identification of protein modifications from protein complexes and lens tissue, *Proc Natl Acad Sci USA* 2002; 99:7900-5; Washburn et al., Analysis of quantitative proteomic data generated via multidimensional protein identification technology, *Anal Chem.* 2002; 74: 16500-7; Washburn et al., Large-scale analysis of the yeast proteome via multidimensional protein identification technology, *Nat. Biotech.* 2001; 19:242-7; Wolters et al., An automated multidimensional protein identification technology for shotgun proteomics, *Anal Chem.* 2001; 73:5683-90; or U.S. Pat. No. 6,800,449; the contents of all of which are incorporated herein by reference.

d. Binding Partner

The β-subunit may be measured by contacting it with a binding partner, which may be capable of specifically binding the β-subunit. The binding partner may be a protein such as an antibody.

(1) Antibody

The antibody may recognize fibrinogen. The antibody may recognize a region of the β-subunit. For example the antibody may recognize a peptide corresponding to a unique or relatively specific region of the β-subunit. The antibody may be affinity purified on a peptide conjugated to BSA. The antibody may be selected from the group consisting of: rabbit polyclonal fibrinogen anti-human antibody (Dako Cat. No. A0080), F4639 monoclonal anti-fibrinogen antibody produced in mouse (Sigma-Aldrich clone FG-21, ascites fluid), F9902 monoclonal anti-fibrinogen antibody produce in mouse (Sigma-Aldrich clone 85D4, ascites fluid), and anti-fibrinogen antibody produced in goat (Sigma-Aldrich clone F8512, whole antiserum.

The antibody may specifically recognize the β-subunit or a region thereof. The specificity of the antibody may be tested by ELISA and Western blotting using a peptide conjugate, or by Western blotting and immunoprecipitation using the β-subunit expressed as a GST fusion protein.

The antibody may be a polyclonal antibody, a single chain antibody (scFv), or a fragment of an antibody. The antibody fragment may be a portion of an intact antibody comprising the antigen binding site or variable region of an intact antibody, wherein the portion is free of the constant heavy chain domains of the Fc region of the intact antibody. The antibody fragment may comprise Fab, Fab', Fab'-SH, F (ab')2, Fv fragments or combination thereof.

The antibody may be a monoclonal antibody, which may be prepared using the β-subunit or fragment thereof and standard hybridoma technology (e.g., Kohler et al., Nature 1975; 256:495; Kohler et al., Eur. J. Immunol. 1976; 6:511; Kohler et al., Eur. J. Immunol. 1976; 6:292; Hammerling et al., In Monoclonal Antibodies and T Cell Hybridomas, Elsevier, New York, N.Y., 1981; Ausubel et al., Current Protocols in Molecular Biology, John Wiley & Sons, New York, N.Y., 1994, the contents of all of which are incorporated herein by reference). The monoclonal antibody may be tested for specific β-subunit recognition by Western blot or immunoprecipitation analysis (by the methods described in Ausubel 1994).

The antibody may also be used to detect an epitope of the β-subunit. Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as the epitope of a β-subunit. Numerous types of competitive binding assays are known, for example: solid phase direct or indirect RIA, solid phase direct or indirect enzyme immunoassay (EIA), sandwich competition assay (see Stahli et al., Methods in Enzymology 1983; 9:242); solid phase direct biotin-avidin EIA (see Kirkland et al., J. Immunol. 1986; 137:3614); solid phase direct labeled assay, solid phase direct labeled sandwich assay (see Harlow and Lane, Antibodies: A Laboratory Manual, Cold Spring Harbor Press, 1988); solid phase direct label RIA using 125I label (see Morel et al., Mol. Immunol. 1988; 25(1):7); solid phase direct biotin-avidin EIA (Cheung et al., Virology 1990; 176:546); and direct labeled RIA. (Moldenhauer et al., Scand. J. Immunol. 1990; 32:77). Such an assay may involve the use of purified antigen bound to a solid surface or cells bearing either of these, an unlabeled test immunoglobulin and a labeled reference immunoglobulin. Competitive inhibition may be measured by determining the amount of label bound to the solid surface or cells in the presence of the test immunoglobulin. The test immunoglobulin may be present in excess. When a competing antibody is present in excess, it may inhibit specific binding of a reference antibody to a common antigen by at least 50-55%, 55-60%, 60-65%, 65-70% 70-75% or more.

An epitope may also be recognized by immunologic cells, for example, B cells and/or T cells. Cellular recognition of an epitope may be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

(2) Label

The binding partner may comprise a label, which may be an atom, moiety, functional group, or molecule which is relied upon to generate or detect a signal attributable to the β-subunit. For example, in a radiochemical assay, the binding partner may be labeled with a radioactive isotope of iodine. Alternatively, the binding partner may be labeled with an enzyme, such as horseradish peroxidase, which can be used in a calorimetric assay. The binding partner may also be labeled with a time-resolved fluorescence reporter. Such reporters are disclosed in Hemmila et al., J. Biochem. Biophys. Methods 1993; 26:283-90; Kakabakos et al., Clin. Chem., 1992; 38:338-42; Xu, Y.-Y., et al., Clin. Chem., 1992; 2038-43; Hemmila et al., Scand. J. Clin. Lab. Invest. 1988; 48:389-400; Hastings et al., Eds., Bioluminescence and Chemiluminescence Proceedings of the 9th International Symposium 1996, Wiley, N.Y., 1996; Knox Van Dyre, Ed., Bioluminescence and Chemiluminescence Instruments and Applications, CRC Press, Boca Raton, 1985; Hemmila, Applications of Fluorescence in Immunoassays, Chemical Analysis, Volume 117, Wiley, N.Y., 1991; and Blackburn et al., Clin. Chem. 1991; 37:1534, the contents of all of which are incorporated herein by reference.

The binding partner may also be labeled with a moiety, functional group, or molecule which is useful for generating a signal in an electrochemiluminescent (ECL) assay. Such moieties, functional groups, or molecules are disclosed in U.S. Pat. Nos. 5,962,218; 5,945,344; 5,935,779; 5,858,676; 5,846,485; 5,811,236; 5,804,400; 5,798,083; 5,779,976; 5,770,459; 5,746,974; 5,744,367; 5,731,147; 5,720,922; 5,716,781; 5,714,089; 5,705,402; 5,700,427; 5,686,244; 5,679,519; 5,643,713; 5,641,623; 5,632,956; 5,624,637; 5,610,075; 5,597,910; 5,591,581; 5,543,112; 5,466,416; 5,453,356; 5,310,687; 5,296,191; 5,247,243; 5,238,808; 5,221,605; 5,189,549; 5,147,806; 5,093,268; 5,068,088; and 5,061,445; and in Dong et al., Anal. Biochem. 1996; 236:344-7; Blohm, et al., Biomedical Products 1996; 21(4):60; Jamieson et al., Anal. Chem. 1996; 68:1298-1302; Kibbey et al., Nature Biotechnology 1997; 14(3):259-260; Yu et al., Applied and Environmental Microbiology 1996; 62(2):587-92; Williams, American Biotechnology 1996; January:26; Darsley et al., Biomedical Products 1996; 21(1):133; Kobrynski et al., Clinical and Diagnostic Laboratory Immunology 1996; 3(1): 42-6; Williams, IVD Technology 1995; November:28-31; Deaver, Nature 1995; 377:758-60; Yu et al., BioMedical Products 1995; 20(10):20; Kibbey et al., BioMedical Products 1995; 20; (9): 116; Schutzbank et al., Journal of Clinical Microbiology 1995; 33:2036-41; Stem et al., Clinical Biochemistry 1995; 28:470-2; Carlowicz, Clinical Laboratory News 1995; 21; (8):1-2; Gatto-Menking et al., Biosensors & Bioelectronics 1995; 10:501-7; Yu et al., Journal of Bioluminescence and Chemiluminescence 1995; 10:239-45; Van Gemen et al., Journal of Virology Methods 1994; 49:157-68; Yang et al., Bio/Technology 1994; 12:193-4; Kenten et al., Clinical Chemistry 1992; 38:873-9; Gudibande et al., Journal of Molecular and Cellular Probes 1992; 6:495-503; Kenten et al., Clinical Chemistry 1991; 37:1626-32; Blackburn; Clinical Chemistry 1991; 37:1534-9; Kenten, "Electrochemiluminescence," Non-radioactive Labeling and Detection of Biomolecules, Kessler, Ed., Springer, Berlin, pp. 175-9, 1992, the contents of all of which are incorporated herein by reference.

The binding partner may also be labeled with a colored latex bead. The preparation of binding partners, such as antibodies, labeled with colored latex beads is well known in the art. Such labeled binding partners may be prepared by diluting latex beads in a solution such as phosphate-buffered saline (8.1 mM $Na_2HPO_4$, 1.5 mM $KH_2PO_4$, 137 mM NaCl, 1.6 mM KCl) and mixing the solution gently to suspend and distribute the latex beads in the solution. About a 10% (wt/v) suspension of latex beads may be diluted about 1:100, to give a suspension of about 0.1% (wt/v) latex beads. A binding partner solution may be added to the latex bead suspension. About 0.3 to about 0.6 mg of the antibody may be added for each mg of latex beads, however, this ratio will vary depending on the specificity and sensitivity of the antibody preparation and the type of support being used. The amount of binding partner to be used for the preparation of the labeled binding partner is derived experimentally using different dilutions of the binding partner preparation. After adding the binding partner, the solution may be gently mixed and incubated at about 4° C. for about 16 to about 20 hours. At the completion of the incubation, the labeled binding partner may be washed with phosphate-buffered saline, and the sensitivity and specificity of the labeled binding partner preparation may be tested.

4. Method of Monitoring Endometriosis

Also provided herein is a method of monitoring endometriosis. A subject may be diagnosed with endometriosis or an endometriosis-related symptom. The endometriosis-related symptom from which the subject is suffering may be changing. The subject may be undergoing treatment for endometriosis or an endometriosis-related symptom. The severity of the endometriosis or endometriosis-related symptom may be difficult to diagnose using a method such as ultrasound. The patient may also be at risk of developing endometriosis. It may therefore be desirable to monitor endometriosis, which may be monitored by measuring the level of fibrinogen β-subunit.

The β-subunit may be detected as described herein. The level of the β-subunit may be compared between samples, collected from the same subject. The samples may have been collected at different times. For example, the samples may have been collected 1-24 hours, 1-5 weeks, 1-12 months, or 1-110 years apart. The level of the β-subunit protein may differ between samples, which may be indicative of a change in endometriosis. For example, an decrease in the level of the β-subunit in a later-collected sample compared to an earlier-collected sample may indicate a worsening of endometriosis. Conversely, an increase between a later- and earlier-collected sample may indicate an improvement in endometriosis. No change between samples collected at different times may indicate a stabilization, lack of improvement, or lack of worsening of endometriosis.

5. Treating Endometriosis

Further provided herein is a method of treating endometriosis. A subject may suffer from endometriosis, and may be undergoing treatment for the disease. It may therefore be desirable to measure the effects of treatment on endometriosios by treating the patient using a method comprising monitoring endometriosis.

6. Kit

Provided herein is a kit, which may be used for diagnosing, monitoring, or treating endometriosis. The kit may comprise a β-subunit binding partner. The kit may also comprise a solid support suitable for binding proteins from a sample. The kit may further comprise a β-subunit composition comprising a β-subunit at a known concentration for use as a positive control. The positive control may be used to measure a threshold or predetermined value.

The kit may also comprise an additional reagent such as a buffer or salt, which may be required for promoting or preventing protein-protein interactions, or removing unbound proteins from a solid support. The kit may further comprise an agent capable of inducing a label on a binding partner to generate a detectable signal. The kit may also comprise an agent capable of stopping a label from generating a signal.

The kit may also comprise one or more containers, such as vials or bottles, with each container containing a separate reagent. The kit may further comprise written instructions, which may describe how to perform or interpret an assay or method described herein.

The present invention has multiple aspects, illustrated by the following non-limiting examples.

EXAMPLES

Example 1

Proteonomic Analysis of Uterine Flushings

Figure 2:
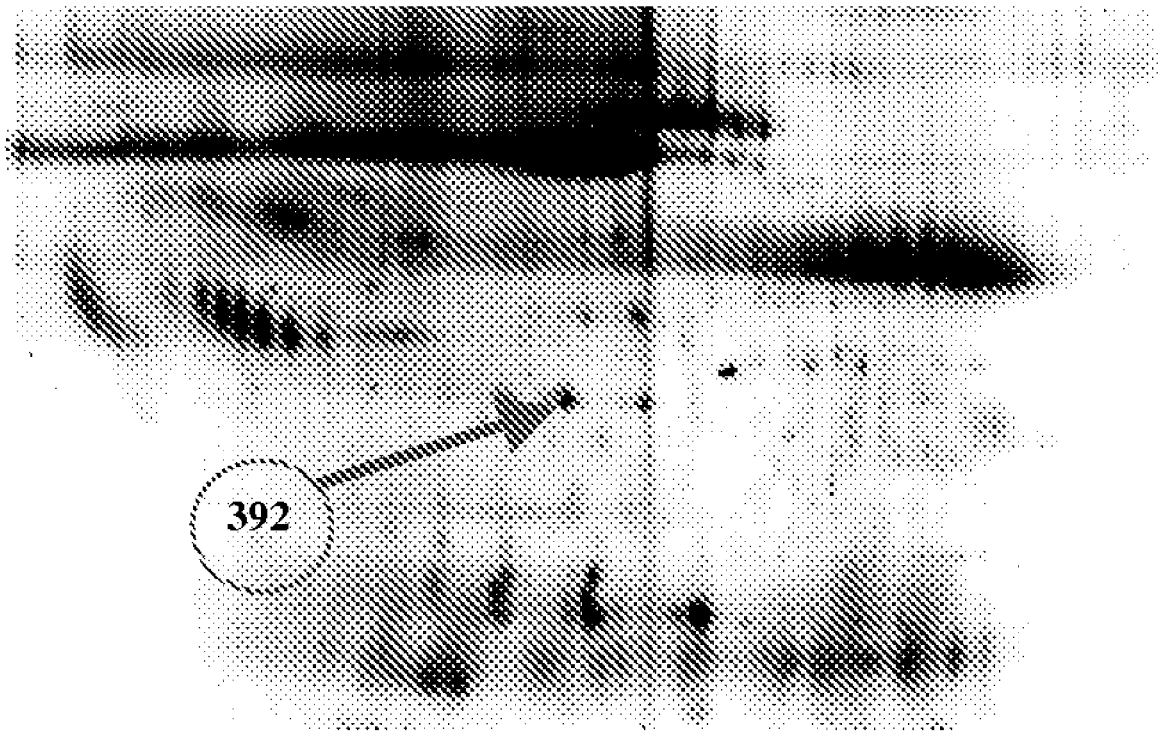
FIG. 2 shows a mass spectroscopy analysis of uterine flushings.
Figure 3:
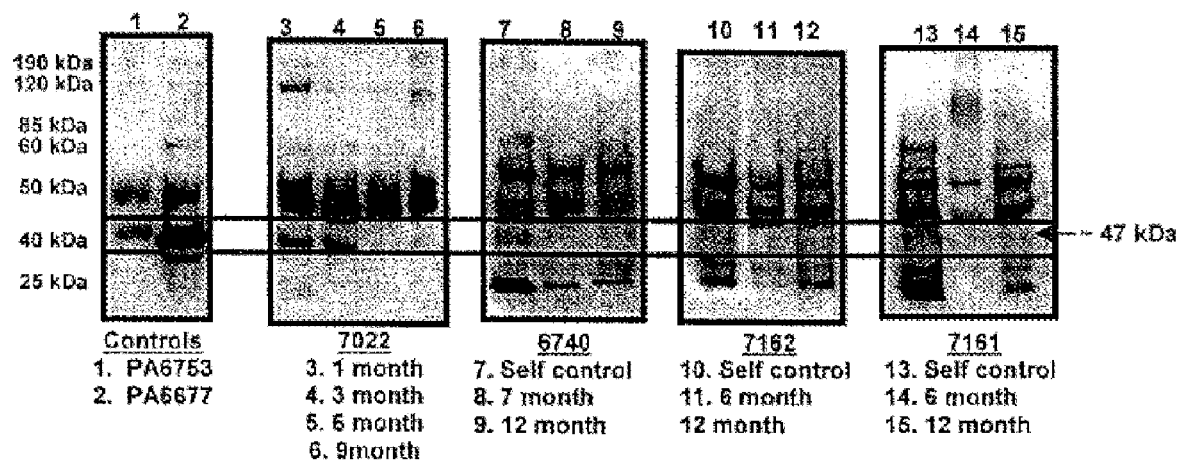
FIG. 3 shows Western blot analysis of uterine flushings.
Figure 3:
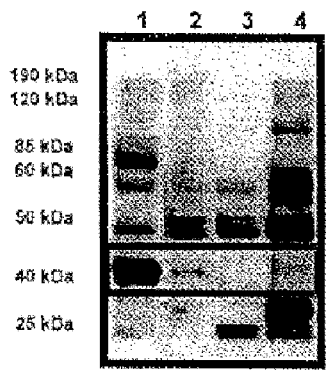

Uterine flushings were evaluated from control baboons and those with endometriosis to determine if changes would be evident that would be reflective of the disease condition. Uterine flushings were obtained at day 10 post ovulation (PO) from baboons with endometriosis (n=3) 1, 3, 6, 9, 12, and 15 months during disease progression. Control flushings were obtained from control animals (n=4) at day 10 PO. Seventy micrograms of protein from each control baboon flush (n=4) was labeled with Cy3; 70 μg of flush protein from baboons with endometriosis (n=3) was labeled with Cy5; the 70 μg of the control flushing that were pooled to serve as a reference standard was labeled with Cy2. The samples were subjected to 2-dimensional (2-D) gel electrophoresis. The first dimension was a pH 3-10 non-linear IPG strip. The second dimension was a 12.5% tris-glycine polyacrylamide gel. Following the 2-D separation, con-imaging of Cy2, Cy3, and Cy5 labeled proteins were subjected to image analysis. A single protein spot was observed to disappear in flushings from baboons with endometriosis between 3 and 6 months of the disease process. See FIG. 1. Mass spectrometry analysis identified this protein spot as the β-subunit of fibrinogen. See FIG. 2. The authenticity of this protein was further confirmed by Western blot analysis of flushings from one of the baboons (PA 7022: FIG. 3, panel 2). Uterine flushings separated on one-dimensional SDS-PAGE gels were incubated with a human polyclonal antibody against fibrinogen. A single band of approximately 47 kD, which corresponds to the β-subunit of fibrinogen was not detectable in the flushes obtained at 6 and 9 months. This confirmed the proteonomic analysis. See FIG. 3.

Flushings from three additional baboons with induced endometriosis were obtained prior to the induction of endometriosis (lanes 7, 10, and 13 of FIG. 3) and additional flushings were obtained at 6 and 12 months following disease induction. These animals served as their own controls. The β-subunit of fibrinogen is present only in the control flushings prior to the induction of the disease but disappears following the establishment of endometriosis. Furthermore, the loss of the β-subunit of fibrinogen was confirmed in baboons with spontaneous disease as well as in flushing from animals during the proliferative stage of the menstrual cycle. These data show that the loss of the β-subunit of fibrinogen may be associated with both spontaneous and induced disease and that this loss may be independent of the stage of the menstrual cycle.

Example 2

Human Protocol

The study will target women undergoing diagnostic laparoscopy for the investigation of pelvic pain or multiparity. On the day of her surgery, the consenting subject will undergo blood sampling (5 ml), cervical secretion collection (with a Dacron swab), a uterine flushing with 15 ml of sterile lactate ringers and an endometrial biopsy. The surgery will be performed while the subject is under anesthesia. During the laparoscopy, confirmation and staging of endometriosis will be performed using the revised ASRM classification scale, and the amount of endometriosis removed/percent of remaining disease will be estimated by the surgeon. Whenever possible, laparoscopic photographs will be taken to confirm the scoring process.

A second group of subjects with the diagnosis of multiparity, who are undergoing laparoscopic tubal ligation, will be used as controls. These subjects will undergo the same type of sample collections and will also be examined to rule out the presence of occult endometriosis. Subjects in the pelvic pain group will have follow-up blood samples (5 ml) and cervical secretions collected as above at 2 weeks, 3 and 6 months post-surgery. Therefore, a total of 4 blood samples, 4 cervical secretion collections with swabs, 1 endometrial biopsy and 1 endometrial flushing will occur during the course of this study.

Subjects in the tubal ligation group will have follow-up blood samples and cervical secretions collected as above at 2 weeks post-surgery and then again at her next regularly scheduled clinic visit. Therefore, a total of 3 blood samples, 3 cervical secretions, 1 endometrial biopsy and 1 uterine flushing will be obtained.

The uterine flushing will be examined for a decrease in the β-subunit, within the uterine flushings of women diagnosed with endometriosis. The cervical swabs will be analyzed to see if this change can also be detected cervically for easier diagnostic applicability. The endometrial biopsy will be analyzed to confirm the subject's phase of the menstrual cycle.

Women, aged 18-51, undergoing diagnostic laparoscopy for pelvic pain or multiparity will be eligible for entry into this study. Eligibility will be assessed by the investigator at the time the subject is being scheduled for surgery. Subjects will be excluded if they are: pregnant, show visual evidence of (or are currently being treated for) cervical or pelvic infection, currently experiencing unexplained uterine bleeding, menopausal or peri-menopausal, or unable to provide informed consent.

A total of 300 subjects will enrolled in this study: 200 patients undergoing diagnostic laparoscopy for pelvic pain and 100 subjects undergoing laparoscopy for multiparity (i.e. tubal ligation). It is estimated that 50% of the subjects with pelvic pain will be positively diagnosed with endometriosis. Of the control subjects undergoing laparoscopy for multiparity, approximately 25% will have occult endometriosis. Therefore, of our 300 subject total, we estimate having 100 subjects with pelvic pain plus endometriosis (experimental group), 75 subjects with no pelvic pain and no endometriosis (control A) and 100 subjects with pelvic pain but no endometriosis (control B).

Control group A represents a pure control where as control group B will be used to rule out any non-specific inflammatory effects associated with pelvic pain but independent of endometriosis. This experimental paradigm is shown in Table 1.

TABLE 2

| Endometriosis | Pelvic Pain | Multiparity | # out of 300 subject total |
|---|---|---|---|
| + | 100 (experimental) | 25 | 125 |
| − | 100 (control B) | 75 (control A) | 175 |

Example 3

ELISA Analysis

Enzyme-linked immunosorbent assay analysis will be performed to detect and quantify the concentration of the β-subunit of fibrinogen in samples. A sandwich ELISA method will make use of anti-β subunit antibodies (capture antibodies), which may be noncovalently adsorbed ("coated"—primarily as a result of hydrophobic interactions) onto plastic microwell plates. After plate washings, the immobilized antibodies may specifically capture soluble β-subunit proteins present in samples that were applied to the plate. After washing away unbound material, the captured proteins are detected by a label-conjugated anti-β subunit antibodies (for example, biotin-labeled detection antibodies) followed by an enzyme-labeled avidin or streptavidin stage. Following the addition of a chromogenic substrate, the level of colored product generated by the bound, enzyme-linked detection reagents may be measured spectrophotometrically using an ELISA-plate reader at an appropriate optical density (OD).

A standard curve may be incorporated into a sandwich ELISA assay by making serial dilutions of a standard β-subunit protein solution of known concentration. Standard curves (aka "calibration curves") are generally plotted as the standard β-subunit protein concentration (typically ng or pg of β-subunit/ml) versus the corresponding mean OD value of replicates. The concentrations of the putative β-subunit-containing samples may be interpolated from the standard curve.

Example 4

2-D Differential and Densitometry Analysis

Uterine flushings from three subjects were collected at different time points ranging from 1 month to 9 months. A total of eight test samples from the three subjects as well as two controls were used in this study.

In preparation for 2D-DIGE test and control samples were cleaned by precipitation with trichloroacetic acid (20%) followed by centrifugation. The resulting protein pellets were washed twice with 300 μL of cold acetone and resolubilized in Cy buffer (30 mM Tris, 8M urea, 4% w/v CHAPS). The final protein concentrations were then quantified using the micro-BCA kit (Pierce). An aliquot containing 70 μg of the test samples from the uterine flushings were labeled with one of two fluorescent dyes (Cy3 and Cy5) from GE Healthcare (Piscataway, N.J.) as noted in Table 1. A pooled control sample containing equal amounts (430 μg) of the two control samples (UF13 and UF16) was prepared and four 70 μg aliquots were labeled with the third Cy dye—Cy2. The differentially-labeled samples were combined as listed Table 3 creating a total of 4 mixtures.

Each sample mixture was then diluted with IPG buffer (8M urea, 2% w/v CHAPS, 2% IPG buffer (GE Healthcare), 0.002% bromophenol blue plus 0.005 g fresh DTT) to a total volume of 350 μL. The mixtures were applied to isoelectric focusing strips (GE Healthcare Immobiline DryStrip, pH=3-10 nonlinear, 18 cm) and separated in the first dimension by isoelectric focusing up to 60,000 V hrs using an IPGPhor unit from GE Healthcare.

The strip was equilibrated for the $2^{nd}$ dimension SDS separation by immersion for 15 minutes into a SDS equilibration buffer (50 mM Tris, 6M urea, 20% glycerol, 2% SDS) containing a reductant (0.5% w/v DTT). The strip was transferred to a hand-cast 12.5% polyacrylamide slab gel (20 cm×26 cm×1.0 mm) and separated by SDS-PAGE using a DALT VI unit (GE Healthcare).

Figure 4:
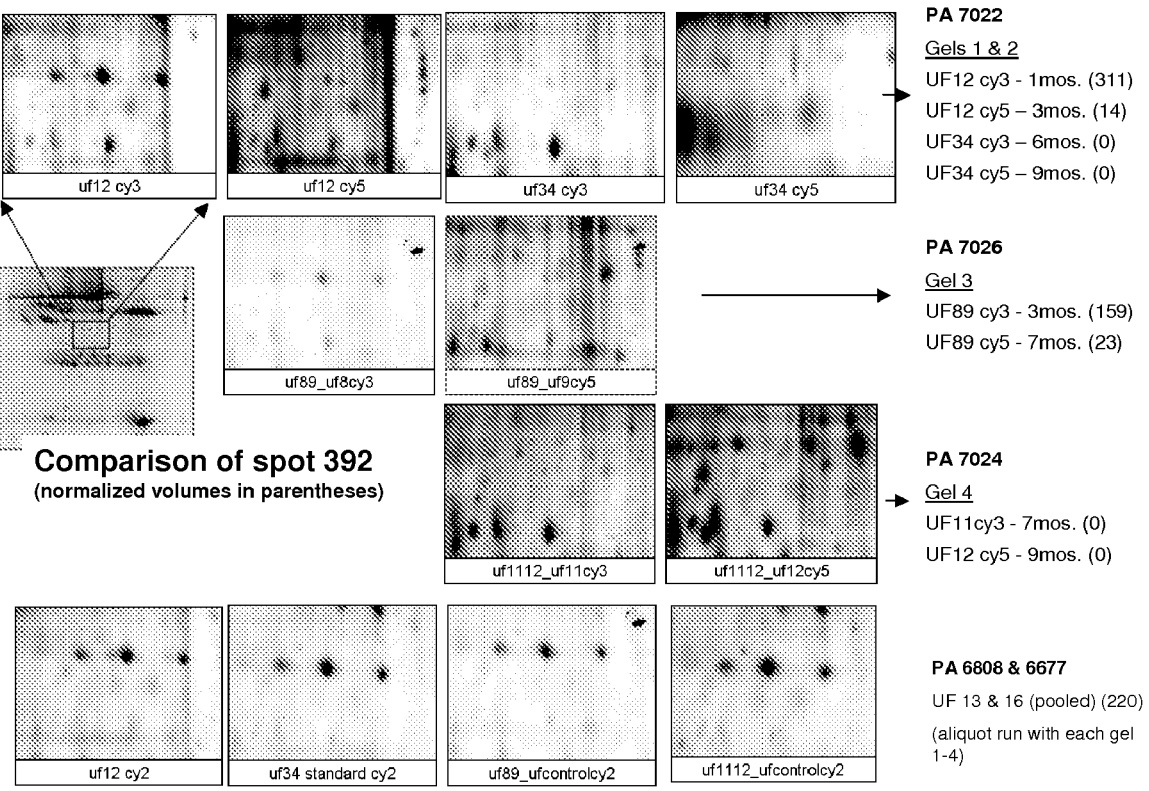
FIG. 4 shows two-dimensional difference gel electrophoresis (2D-DIGE) and densitometry analysis of uterine flushings from baboons.

Images for the Cy2, Cy3 and Cy5 labeled proteins within each gel were obtained separately using a fluorescent imager (ProXpress, Perkin-Elmer, Wellesley, Mass.). See FIG. 4. The images were analyzed by Progenesis Discovery software (Nonlinear Dynamics, Newcastle upon Tyne, UK). For these analyses the samples obtained at later time points (Cy5 labeled) were compared to an earlier time point (Cy3 labeled) for a given subject. Using this logic the following samples were compared: Subject PA 7022 3 months vs. 1 month, Subject PA 7022 9 months vs. 6 months, Subject PA 7026 7 months vs. 3 months, Subject PA 7024 9 months vs. 7 months.

Gel number 1 was post-stained with Sypro Ruby (Invitrogen, Carlsbad, Calif.), imaged for Sypro Ruby fluorescence and analyzed by the Progenesis Discovery software. The protein of interest as determined by the DIGE analysis was located and its x- and y-coordinates was then input into the BioMachines 2DiD gel-cutting robot. The excised gel spot was in-gel digested with trypsin using a ProGest digestor (Genomics Solutions, Ann Arbor, Mich.) using our standard method for identification of gel-separated proteins and analysed by matrix-assisted laser desorption ionization time-of-flight tandem mass spectrometry (MALDI-TOF/TOF). MALDI/TOF/TOF spectra were acquired on an ABI 4700 Proteomics Analyzer mass spectrometer (Applied Biosystems, Foster City, Calif.), using the trypsin autolysis products for internal calibration. The mass spectrometer was set to acquire 15 MS/MS spectra from each spot. The data (MS and MS/MS data) was then automatically searched against the MSDB database, using ABI's GPS Explorer database search engine based on the Mascot database search software (Matrix Science, Boston, Mass.). Parameters for the search query include a peptide mw tolerance of 80 ppm, and an MS/MS fragment ion tolerance of 0.1 Da. Peptides in the +1 charge states were included in the searches. Proteins with scores above the Mascot probability-based scoring threshold are reported as "hits".

TABLE 3

|  |  | Sample # | Label | Gel # |
|---|---|---|---|---|
| PA 7022 | 1 month | UF1 | Cy3 | 1 |
|  | 3 months | UF2 | Cy5 |  |
|  |  | Controls | Cy2 |  |

TABLE 3-continued

|  |  | Sample # | Label | Gel # |
|---|---|---|---|---|
| PA 7022 | 6 months | UF3 | Cy3 | 2 |
|  | 9 months | UF4 | Cy5 |  |
|  |  | Controls | Cy2 |  |
| PA 7026 | 3 months | UF8 | Cy3 | 3 |
|  | 7 months | UF9 | Cy5 |  |
|  |  | Controls | Cy2 |  |
| PA 7024 | 7 months | UF11 | Cy3 | 4 |
|  | 9 months | UF12 | Cy5 |  |
|  |  | Controls | Cy2 |  |

I claim:

1. A method for diagnosing endometriosis in a subject, comprising:
    (a) providing a sample isolated from the subject; and
    (b) measuring the level of fibrinogen β-subunit in the sample;
    wherein a level of fibrinogen β-subunit lower than the level of a control is indicative of endometriosis.

2. The method of claim 1, wherein the level of fibrinogen β-subunit is between 0 and 95% of the level of the control.

3. The method of claim 2, wherein the level of fibrinogen β-subunit is between 0 and 70% lower than the control.

4. The method of claim 1, wherein measuring the level of fibrinogen β-subunit comprises contacting fibrinogen β-subunit with a fibrinogen β-subunit binding partner.

5. The method of claim 4, wherein the binding partner is an antibody.

6. The method of claim 5, wherein the antibody is monoclonal.

7. The method of claim 6, wherein the antibody is selected from the group consisting of: rabbit polyclonal fibrinogen anti-human antibody (Dako Cat. No. A0080), F4639 monoclonal anti-fibrinogen antibody produced in mouse (Sigma-Aldrich clone FG-21, ascites fluid), F9902 monoclonal anti-fibrinogen antibody produce in mouse (Sigma-Aldrich clone 85D4, ascites fluid), and anti-fibrinogen antibody produced in goat (Sigma-Aldrich clone F8512, whole antiserum).

8. The method of claim 4, wherein the binding partner further comprises a label.

9. The method of claim 1, wherein the level of fibrinogen β-subunit is measured using a detection method selected from the group consisting of: Western blot, two-dimensional gel electrophoresis, mass spectrometry (MS), tandem mass spectrometry, and multiple rounds of mass spectrometry.

10. The method of claim 9, wherein the mass spectrometry comprises using a mass analyzer.

11. The method of claim 10, wherein the mass analyzer is selected from the group consisting of: ion trap, triple quadrupole, time-of-flight, quadrupole-time-of-flight mass spectrometry, and Fourier transform ion cyclotron mass spectrometry (FT-ICR-MS).

12. The method of claim 10, wherein the mass spectrometry further comprises a matrix-assisted laser desorption (MALDI) or electrospray ionization (ESI) ion source.

13. The method of claim 1, wherein the subject is a mammal.

14. The method of claim 13, wherein the mammal is a human.

15. The method of claim 1, wherein the sample is selected from the group consisting of: blood, lymph fluid, ascetic fluid, gynecological fluid, urine, peritoneal fluid, cerebrospinal fluid, a fluid collected by vaginal rinsing, and a fluid collected by vaginal flushing.

* * * * *

SEQUENCE LISTING

<160> NUMBER OF SEQ ID NOS: 1

<210> SEQ ID NO 1
<211> LENGTH: 491
<212> TYPE: PRT
<213> ORGANISM: Homo sapiens

<400> SEQUENCE: 1

```
Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
                20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
        50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
    210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255
```

-continued

```
Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
    290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
            325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
            355                 360                 365

Gln Ile Ser Val Asn Lys Tyr Arg Gly Thr Ala Gly Asn Ala Leu Met
    370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
            405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
            485                 490
```